(12) United States Patent
Muthaiyyan et al.

(10) Patent No.: US 12,280,062 B2
(45) Date of Patent: Apr. 22, 2025

(54) PARENTERAL COMPOSITIONS COMPRISING METHYLENE BLUE

(71) Applicant: CADILA HEALTHCARE LIMITED, Gujarat (IN)

(72) Inventors: Kannan Essakimuthu Muthaiyyan, Gujarat (IN); Debjani Manoj Singh, Gujarat (IN); Tushar Surajmal Nahata, Gujarat (IN); Pradeep Jawarchand Chouhan, Gujarat (IN); Bhaveshkumar Ravishankar Shah, Gujarat (IN); Parth Dhirajkumar Thakkar, Gujarat (IN)

(73) Assignee: ZYDUS LIFESCIENCES LIMITED, Gandhinagar (IN)

( * ) Notice: Subject to any disclaimer, the term of this patent is extended or adjusted under 35 U.S.C. 154(b) by 0 days.

(21) Appl. No.: 17/677,437

(22) Filed: Feb. 22, 2022

(65) Prior Publication Data

US 2022/0265674 A1    Aug. 25, 2022

(30) Foreign Application Priority Data

Feb. 24, 2021 (IN) .............................. 202121007686

(51) Int. Cl.
| | | |
|---|---|---|
| *A61K 31/5415* | (2006.01) | |
| *A61K 9/00* | (2006.01) | |
| *A61K 9/08* | (2006.01) | |
| *A61K 45/06* | (2006.01) | |
| *A61K 47/12* | (2006.01) | |

(52) U.S. Cl.
CPC ........ *A61K 31/5415* (2013.01); *A61K 9/0019* (2013.01); *A61K 9/08* (2013.01); *A61K 45/06* (2013.01); *A61K 47/12* (2013.01)

(58) Field of Classification Search
CPC ....... A61K 31/5415; A61K 9/08; A61K 45/06
See application file for complete search history.

(56) References Cited

U.S. PATENT DOCUMENTS 9,675,621 B2    6/2017 Wischik et al.
2007/0286881 A1 * 12/2007 Burkinshsw ......... A61K 38/363
                                                              424/94.64

FOREIGN PATENT DOCUMENTS

| WO | WO-0185249 A1 * | 11/2001 | ............. A61L 29/14 |
| WO | WO-2008019083 A2 * | 2/2008 | ............. A01N 37/40 |
| WO | WO-2020250186 A1 * | 12/2020 | ........... C07D 279/18 |

OTHER PUBLICATIONS (Provayblue®) Highlights of Prescribing Information https://www.accessdata.fda.gov/drugsatfda_docs/label/2017/204630s005lbl.pdf (Year: 2016).*
Australian Product Information—Methylene Blue Injection https://www.phebra.com/wp-content/uploads/2018/10/Methylene-Blue-PI-V02.pdf (Year: 2019).*
International Journal of Toxicology, 20(Suppl.3):23-50, 2001. (Year: 2001).*
Diakogiannis I, et al. Growth and membrane fluidity of food-borne pathogen *Listeria monocytogenes* in the presence of weak acid preservatives and hydrochloric acid. Front Microbiol. Jun. 14, 2013;4:152. doi: 10.3389/fmicb.2013.00152. (Year: 2013).*
H. Hurley, et al. (Dye Clearance and Eccrine Sweat Secretion in Human Skin*, Journal of Investigative Dermatology, vol. 36, Issue 4, 1961, pp. 259-272, ISSN 0022-202X, doi.org/10.1038/jid.1961.44. (Year: 1961).*
Provayblue® (methylene blue) injection USP (2016). (Year: 2016).*
Provayblue® Label by Provepharm, Reference IDS 4800624, 10 pgs.

* cited by examiner

*Primary Examiner* — Medhanit W Bahta
*Assistant Examiner* — Manahil Mirghani Ali Abdalhameed
(74) *Attorney, Agent, or Firm* — NIXON & VANDERHYE, PC

(57) ABSTRACT

The present invention relates to parenteral compositions comprising methylene blue, water and one or more pH regulating agents. The present invention also relates to processes for preparing such compositions.

7 Claims, No Drawings

PARENTERAL COMPOSITIONS COMPRISING METHYLENE BLUE

This application claims priority to IN patent application No. 202121007686 filed Feb. 24, 2021, the entire contents of which are hereby incorporated by reference.

FIELD OF THE INVENTION

The present invention relates to parenteral compositions comprising methylene blue, water and one or more pH regulating agents. The present invention also relates to processes for preparing such compositions.

BACKGROUND OF THE INVENTION

Methylene blue is also known as methylthioninium chloride (MTC), methylthionine chloride or tetramethylthionine chloride. Chemical name of methylene blue is 3,7-bis(dimethylamino) phenothiazin-5-ium, chloride which is having the formula as mentioned below:

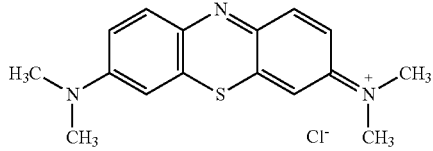

U.S. Pat. No. 9,675,621 discloses high purity Methylthioninium Chloride (MTC) (Methylene Blue) and pharmaceutical compositions thereof. It also mentions formulations suitable for parenteral administration (e.g., by injection) which may be aqueous or non-aqueous, isotonic, pyrogen-free, sterile liquids (e.g., solutions, suspensions). It also discloses that the formulations may be presented in unit-dose or multi-dose sealed containers, for example, ampoules and vials, and may be stored in a freeze-dried (lyophilized) conditions requiring only the addition of sterile liquid carrier, for example water for injection, immediately prior to use.

Methylene blue injectable solution USP, for intravenous use, is marketed in USA under the brand name Provayblue® by Provepharm SAS in the strength of 50 mg/10 mL (5 mg/mL).

There still exists a need for an alternate stable parenteral solution comprising methylene blue.

SUMMARY OF THE INVENTION

In one general aspect, the present invention provides parenteral compositions comprising methylene blue, water and one or more pH regulating agents.

In another general aspect, the present invention provides process for preparing the parenteral composition comprising methylene blue, water and one or more pH regulating agents.

In another general aspect, the present invention provides a method for the treatment of methemoglobinemia in a patient in need thereof comprising administering a parenteral solution comprising methylene blue, water and one or more pH regulating agents.

The details of one or more embodiments of the invention are set forth in the description below. Other features, objects and advantages of the invention will be apparent from the description.

DETAILED DESCRIPTION OF THE INVENTION

The inventors of the invention have discovered that a stable parenteral solution comprising methylene blue can be prepared using water and one or more pH regulating agents.

The present invention provides a parenteral composition comprising methylene blue, one or more pH regulating agents and water.

In one embodiment, the present invention provides a pharmaceutical composition in the form of a parenteral solution.

The term "parenteral solution" as used herein, unless explicitly stated otherwise, means a solution for administration through parenteral route. In particular, parenteral solution is a solution for administration through intravenous, subcutaneous and/or intramuscular route and it does not include solution for administration through other routes viz., oral, topical, nasal and ophthalmic route etc.

The term "one or more pH regulating agents" as used herein, unless explicitly stated otherwise, means at least one pharmaceutical excipient selected from the group consisting of an antioxidant, a buffer and a preservative, which can modify and/or maintain a predetermined pH or pH range of a solution.

Examples of suitable antioxidants for the parenteral solution may include, but not limited to, monothioglycerol, ascorbic acid, 1-cysteine, sodium bisulfite, disodium edetate, or any combination thereof.

Examples of suitable buffers for the parenteral solution may include, but not limited to, acetate buffer (e.g. sodium acetate trihydrate and acetic acid etc.), citrate buffer (e.g. anhydrous citric acid and trisodium citrate dihydrate etc.), or any combination thereof.

Examples of suitable preservatives may include, but not limited to, benzoic acid.

In another embodiment, the present invention provides a parenteral solution comprising methylene blue, water and one or more pH regulating agents, wherein the solution has a pH of between 3 and 4.5.

In another embodiment, the present invention provides a parenteral solution comprising methylene blue, water and one or more pH regulating agents, wherein the solution has a pH of between 3 and 4.5, and wherein methylene blue is the sole active ingredient present in the solution.

In another embodiment, the present invention provides a parenteral solution comprising methylene blue, water and one or more pH regulating agents, wherein the solution has a pH of between 3 and 4.5, wherein the pH regulating agent is a buffer.

In another embodiment, the present invention provides a parenteral solution comprising methylene blue, water and one or more pH regulating agents, wherein the solution has a pH of between 3 and 4.5, wherein the pH regulating agent is an antioxidant.

In another embodiment, the present invention provides a parenteral solution comprising methylene blue, water and one or more pH regulating agents, wherein the solution has a pH of between 3 and 4.5, wherein the pH regulating agent is a preservative.

In another embodiment, the present invention provides a parenteral solution comprising methylene blue, water, anhydrous citric acid and trisodium citrate dihydrate.

In one embodiment, the present invention provides a process for preparing a parenteral solution comprising methylene blue, water and one or more pH regulating agents. The process includes steps of: (a) adding and dissolving one or more pH regulating agents in 90% of water for injection, (b) adding and dissolving methylene blue to the solution prepared in step (a) and making volume up to the batch size with water for injection. Additionally, the process may include filtering the solution using PES (Polyethersulfone) filter and filling aseptically into the glass vials. The filled vials may be further stoppered and sealed with aluminium flip-off seals. Additionally, the process may include terminal sterilization of the sealed vials.

In another embodiment, the present invention provides a process for preparing a parenteral solution comprising methylene blue, water, anhydrous citric acid and trisodium citrate dihydrate. The process includes steps of: (a) adding and dissolving trisodium citrate dihydrate to 90% of water for injection, (b) adding and dissolving anhydrous citric acid to the solution prepared in step (a), and (c) adding and dissolving methylene blue to the solution prepared in step (b) and making volume up to the batch size with water for injection. Additionally, the process may include filtering the solution using 0.8 micron+0.2 micron PES (Polyethersulfone) filter and filling aseptically into the glass vials. The filled vials may be further stoppered and sealed with aluminium flip-off seals. Additionally, the process may include terminal sterilization of the sealed vials.

In one embodiment, the present invention provides a method for the treatment of methemoglobinemia in a patient in need thereof comprising administering a parenteral solution comprising methylene blue, water and one or more pH regulating agents.

In another embodiment, the present invention provides a parenteral solution for administration through intravenous, subcutaneous and/or intramuscular route.

In one embodiment, the present invention provides a parenteral solution comprising methylene blue and citrate as a buffer, wherein the citrate is present as a mixture of anhydrous citric acid and trisodium citrate dihydrate.

In another embodiment, the present invention provides a parenteral solution comprising methylene blue, one or more pH regulating agents and one or more pharmaceutically acceptable excipients.

The suitable pharmaceutically acceptable excipients for the parenteral solution of the present invention may include one or more solvents and isotonicity adjusting agents.

Examples of suitable pharmaceutically acceptable solvents for the parenteral solution of the present invention may include, but not limited to, water for injection, and the like.

Examples of suitable isotonicity adjusting agents for the parenteral solution may include, but not limited to, sodium chloride, potassium chloride, calcium chloride, magnesium chloride, glucose, sucrose, dextrose, mannitol, glycerol, or any combination thereof.

In another embodiment, the present invention provides a parenteral solution, wherein the solution does not contain any organic solvent.

In one embodiment, the present invention provides a parenteral solution comprising methylene blue, water and one or more pH regulating agents, wherein methylene blue is present in a concentration of about 5 mg/mL.

In another embodiment, the present invention provides a parenteral solution comprising methylene blue, water and a citrate buffer, wherein the citrate buffer is present as a mixture of anhydrous citric acid and trisodium citrate dihydrate, wherein the trisodium citrate dihydrate is present in a concentration of from about 0.01 mg/mL to about 0.30 mg/mL, for example, 0.05 mg/mL, 0.10 mg/mL, 0.15 mg/mL, 0.20 mg/mL, or 0.25 mg/mL.

In another embodiment, the present invention provides a parenteral solution comprising methylene blue, water and a citrate buffer, wherein the citrate is present as a mixture of anhydrous citric acid and trisodium citrate dihydrate, wherein the anhydrous citric acid is present in a concentration of from about 0.01 mg/mL to about 0.50 mg/mL, for example, 0.05 mg/mL, 0.10 mg/mL, 0.15 mg/mL, 0.20 mg/mL, 0.25 mg/mL, 0.30 mg/mL, 0.35 mg/mL, 0.40 mg/mL, or 0.45 mg/mL.

In one embodiment, the present invention provides a parenteral solution comprising methylene blue, water and one or more pH regulating agents, wherein the solution has a pH of between 3.0 and 4.5, for example, between 3.60 and 3.75.

In another embodiment, the present invention provides a parenteral solution comprising 5 mg/mL methylene blue, 0.1 mg/mL anhydrous citric acid, 0.05 mg/mL trisodium citrate dihydrate and up to 1 mL water.

In another embodiment, the present invention provides a parenteral solution comprising 5 mg/mL methylene blue, 0.1 mg/mL anhydrous citric acid, 0.05 mg/mL trisodium citrate dihydrate and up to 1 mL water, wherein (a) the solution has a pH of between 3.0 and 4.5, for example, between 3.60 and 3.75, (b) methylene blue is the sole active ingredient present in the solution; and (c) the solution does not contain any organic solvent.

In another embodiment, the parenteral solution comprising methylene blue, water and one or more pH regulating agents remains stable after storage of solution in USP type-1 clear tubular glass vials, 20 mm rubber stopper and 20 mm aluminum flip-off seal.

In another embodiment, the present invention provides a stable parenteral solution comprising methylene blue, water and one or more pH regulating agents, wherein the stable parenteral solution may retain at least 95% of methylene blue (% assay) initially or after storage for at least 6 months at 40° C./75% RH or 30° C./65% RH, and at least for 24 months at 25° C./60% RH.

In another embodiment, a stable parenteral solution comprising methylene blue, water and one or more pH regulating agents is clear (free of any particulate matter) by visual inspection.

In another embodiment, a stable parenteral solution comprising methylene blue in a concentration 5 mg/mL, water and one or more pH regulating agents is further diluted 5000 times with water for injection and tested for its absorbance at 420 nm, wherein the diluted parenteral solution provides the value of absorbance not more than 0.10 AU, for example, 0.09 AU, 0.08 AU, 0.06 AU, 0.04 AU, 0.02 AU, or 0.01 AU.

In another embodiment, a stable parenteral solution comprising methylene blue in a concentration 5 mg/mL, water and one or more pH regulating agents is further diluted 5000 times with water for injection and tested for its % transmittance, wherein the diluted parenteral solution provides the value of % transmittance not less than 97.0%, for example, not less than 98.0%, not less than 99.0%, not less than 99.2%, not less than 99.4%, not less than 99.8%, or not less than 99.9%.

In another embodiment, the stable parenteral solution comprising methylene blue either does not contain an Azure A impurity (7-aminophenothiazin-3-ylidene)-dimethylazanium chloride) or if contain, the Azure A impurity is present in an amount of not more than 0.20%, for example, not more than 0.15%, not more than 0.1%, not more than 0.07%, not more than 0.05%, or not more than 0.03%, by weight of methylene blue, as determined by HPLC initially or after storage for at least 6 months at 40° C./75% RH or 30° C./65% RH, and at least for 24 months at 25° C./60% RH.

In another embodiment, the stable parenteral solution comprising methylene blue may contain an Azure B impurity (dimethyl-[7-(methylamino)phenothiazin-3-ylidene] azanium chloride), wherein the solution does not contain Azure B impurity more than 3.0%, for example, more than 2.8%, more than 2.7%, more than 2.6%, more than 2.5%, more than 2.4%, more than 2.3%, or more than 2.2%, by weight of methylene blue, as determined by HPLC initially or after storage for at least 6 months at 40° C./75% RH or 30° C./65% RH, and at least for 24 months at 25° C./60% RH. In another embodiment, limit of Azure B impurity (%) is between 2.1% and 3.0%, by weight of methylene blue, as determined by HPLC initially or after storage for at least 6 months at 40° C./75% RH or 30° C./65% RH, and at least for 24 months at 25° C./60% RH.

In another embodiment, the stable parenteral solution comprising methylene blue either does not contain an Azure C impurity (7-methyliminophenothiazin-10-ium-3-amine chloride) or if contain, the Azure C impurity is present in an amount of not more than 0.20%, for example, not more than 0.15%, not more than 0.1%, not more than 0.07%, not more than 0.05%, or not more than 0.03%, by weight of methylene blue, as determined by HPLC initially or after storage for at least 6 months at 40° C./75% RH or 30° C./65% RH, and at least for 24 months at 25° C./60% RH.

In another embodiment, the stable parenteral solution comprising methylene blue, water and one or more pH regulating agents does not contain total impurities (including Azure B) more than 5.0%, for example, more than 4%, more than 3%, more than 2%, or more than 1%, by weight of methylene blue, as determined by HPLC initially or after storage for at least 6 months at 40° C./75% RH or 30° C./65% RH, and at least for 24 months at 25° C./60% RH.

In another embodiment, the stable parenteral solution comprising methylene blue, water and one or more pH regulating agents may have osmolality value of between about 5 mOsm/kg and about 20 mOsm/kg, for example, between about 10 mOsm/kg and about 15 mOsm/kg, for example, 7 mOsm/kg, 9 mOsm/kg, 10 mOsm/kg, 13 mOsm/kg, 15 mOsm/kg, or 17 mOsm/kg.

In another embodiment, the stable parenteral solution comprising methylene blue, water and one or more pH regulating agents may have a pH of between 3 and 4.5, for example, 3.1, 3.2, 3.3, 3.4, 3.5, 3.6, 3.7, 3.8, 3.9, 4.0, 4.1, 4.2, 4.3, or 4.4.

The term "stable" as used herein, refers to any parenteral solution comprising a drug having sufficient physical and chemical stability to allow storage at a convenient temperature, such as from about 0° C. to about 40° C., for a commercially reasonable period of time. The term "physical stability" refers to maintenance of color or colorless state, and particulate matter content. The term "chemical stability" relates to formation of the drug-related impurities in terms of total impurities, known impurities and single maximum unknown impurity, up to allowed limits by the Regulatory Agency. For pharmaceutical products, stability is required for commercially relevant time points after manufacturing, such as for about 1, 3, 6, 12, 18, or 24 months, during which a product is kept in its original packaging under specified storage conditions.

The term "about" as used herein, refers to encompass +/−20%, 15%, 10%, 5%, 2%, 1%, 0.5%, or 0.25% of the numerical value of the number with which it is being used.

Abbreviations:

μg/g: Microgram per gram
mg: Milligram
mm: Millimeter
mL: Millilitre
ND: Not Detected.
BQL: Below Quantification Limit
RH: Relative Humidity
° C.: Degree Centigrade/Celsius
NMT: Not More Than
NLT: Not Less Than
q.s.: Quantity Sufficient
AU: Absorbance Units
mOsm/kg: Milliosmoles Per Kilogram
HPLC: High-performance liquid chromatography The present invention is illustrated by the following examples which are provided to be exemplary of the invention and do not limit the scope of the invention.

Example 1

TABLE 1

| Sr. no. | Ingredients | Quantity |
|---|---|---|
| 1 | Methylene blue | 5 mg/mL |
| 2 | Sodium citrate, Dihydrate (trisodium citrate dihydrate) | 0.05 mg/mL |
| 3 | Anhydrous citric acid | 0.10 mg/mL |
| 4 | Water for injection (WFI) | q.s. to 1 mL |

Batch size: 2000 mL

Process:

1. Water for injection, approximately 90% of the batch size, was taken in compounding vessel.

2. Sodium citrate dihydrate (dispensed quantity) was added to the water for injection collected in the compounding vessel and dissolved.

3. Anhydrous citric acid (dispensed quantity) was added to the step 2 and dissolved.

4. Methylene blue (dispensed quantity) was added to the step 3 and dissolved.

5. Volume of the bulk solution was made up to 100% of the batch size with water for injection and stirred for 10 minutes.

6. The pH of the solution was checked at the end of compounding. In the experiments, the pH observed was 3.60-3.75 (limit: 3.0-4.5).

7. The above bulk solution was filtered using 0.8 micron+ 0.2 micron PES filter and filled into 10 mL clear USP type I glass vial.

8. The filled vials were stoppered and sealed with aluminum flip-off seals.

9. The sealed vials were terminally sterilized at 121° C. for 15 minutes.

10. The product is light sensitive, so dispensing, manufacturing, filling and capping was done under non-actinic light.

The solution prepared according to above Example 1 (Methylene blue solution for Injection USP, 5 mg/mL; 10 mL) was tested for its physical stability and chemical stability, and the results are reported in Table 2 below.

TABLE 2

| Storage condition | Parameter | Initial | 6 months storage | |
|---|---|---|---|---|
| | | | Inverted vial position | Upright vial position |
| 40° C./75% RH | Description | Clear dark blue solution | Clear dark blue solution | Clear dark blue solution |
| | pH | 3.80 | 3.81 | 3.80 |
| | Osmolality (mOsm/kg) | 13 | 11 | 12 |
| | Assay (%) | 100.7 | 99.0 | 99.2 |
| | Organic impurities (By HPLC) | | | |
| | Azure B (%) | 2.4 | 2.6 | 2.6 |
| | Azure A (%) | 0.05 | 0.08 | 0.08 |
| | Azure C (%) | ND | ND | ND |
| | Total impurities (Including Azure B) (%) | 2.6 | 2.7 | 2.7 |
| | pH | 3.80 | 3.81 | 3.82 |
| | Osmolality (mOsm/kg) | 13 | 12 | 12 |
| | Assay (%) | 100.7 | 99.2 | 99.6 |
| | Organic impurities (By HPLC) | | | |
| | Azure B (%) | 2.4 | 2.6 | 2.5 |
| | Azure A (%) | 0.05 | 0.08 | 0.08 |
| | Azure C (%) | ND | ND | ND |
| | Total impurities (Including Azure B) (%) | 2.6 | 2.7 | 2.6 |

| Storage condition | Parameter | Initial | 24 months storage | |
|---|---|---|---|---|
| | | | Inverted vial position | Upright vial position |
| 25° C./60% RH | Description | Clear dark blue solution | Clear dark blue solution | Clear dark blue solution |
| | pH | 3.80 | 3.88 | 3.87 |
| | Osmolality (mOsm/kg) | 13 | 12 | 12 |
| | Assay (%) | 100.7 | 99.6 | 99.9 |
| | Organic impurities (By HPLC) | | | |
| | Azure B (%) | 2.4 | 2.7 | 2.6 |
| | Azure A (%) | 0.05 | 0.08 | 0.09 |
| | Azure C (%) | ND | ND | ND |
| | Total impurities (Including Azure B) (%) | 2.6 | 2.8 | 2.7 |

The solution prepared according to above Example 1 (Methylene blue solution for Injection USP, 5 mg/mL; 10 mL) was diluted 5000 times with water for injection and tested for its % transmittance and absorbance, and the results are reported in Table 3 below.

TABLE 3

| Storage condition | Parameter | Initial | 6 months storage | |
|---|---|---|---|---|
| | | | Inverted vial position | Upright vial position |
| 40° C./75% RH | % transmittance | 99.9 | 99.5 | 99.5 |
| | Absorbance at 420 nm | 0.001 | 0.002 | 0.002 |
| | Absorbance at 420 nm | 0.001 | 0.001 | 0.001 |

| | Parameter | Initial | 24 months storage | |
|---|---|---|---|---|
| | | | Inverted vial position | Upright vial position |
| 25° C./60% RH | % transmittance | 99.9 | 99.8 | 99.8 |
| | Absorbance at 420 nm | 0.001 | 0.001 | 0.001 |

The invention claimed is:

1. A parenteral solution consisting of methylene blue, water, and a citrate buffer, wherein the parenteral solution has a pH of between 3 and 4.5, wherein the parenteral solution is for administration through intravenous, subcutaneous and/or intramuscular route, wherein the methylene blue is present in a concentration of about 5 mg/ml; and the citrate buffer comprises a mixture of anhydrous citric acid and trisodium citrate dihydrate, wherein the trisodium citrate dihydrate is present in a concentration of from about 0.01 mg/ml to about 0.10 mg/ml and the anhydrous citric acid is present in a concentration of from 0.05 mg/ml to about 0.20 mg/ml.

2. The parenteral solution according to claim 1, wherein the trisodium citrate dihydrate is present in a concentration of about 0.05 mg/mL.

3. The parenteral solution according to claim 1, wherein the anhydrous citric acid is present in a concentration of about 0.10 mg/mL.

4. The parenteral solution according to claim 1, wherein the parenteral solution has osmolality value of between 10 mOsm/kg and 15 mOsm/kg.

5. The parenteral solution according to claim 1, wherein the parenteral solution has % transmittance value not less than 97.0% and absorbance value not more than 0.10 AU.

6. A process for preparing a parenteral solution consisting of methylene blue, water, and a citrate buffer, process comprising: (a) adding and dissolving the citrate buffer in water, and (b) adding and dissolving methylene blue to the solution prepared in step (a), wherein the parenteral solution has a pH of between 3 and 4.5 and is for administration through intravenous, subcutaneous and/or intramuscular route, wherein the methylene blue is present in a concentration of about 5 mg/ml; and the citrate buffer comprises a mixture of anhydrous citric acid and trisodium citrate dihydrate, wherein the trisodium citrate dihydrate is present in a concentration of from about 0.01 mg/ml to about 0.10 mg/ml and the anhydrous citric acid is present in a concentration of from 0.05 mg/ml to about 0.20 mg/ml.

7. A method for treatment of methemoglobinemia comprising administering through an intravenous, subcutaneous and/or intramuscular route to a patient in need thereof a parenteral solution consisting of methylene blue, water, and a citrate buffer, wherein the parenteral solution has a pH of between 3 and 4.5, wherein the methylene blue is present in a concentration of about 5 mg/ml; and the citrate buffer comprises a mixture of anhydrous citric acid and trisodium citrate dihydrate, wherein the trisodium citrate dihydrate is present in a concentration of from about 0.01 mg/ml to about 0.10 mg/ml and the anhydrous citric acid is present in a concentration of from 0.05 mg/ml to about 0.20 mg/ml.

* * * * *